United States Patent [19]

Evans

[11] Patent Number: 4,687,779

[45] Date of Patent: Aug. 18, 1987

[54] CHROMANOL DERIVATIVES

[75] Inventor: John M. Evans, Roydon, England

[73] Assignee: Beecham Group p.l.c., England

[21] Appl. No.: 645,492

[22] Filed: Aug. 29, 1984

[30] Foreign Application Priority Data

Sep. 1, 1983 [GB] United Kingdom ................ 8323417
Dec. 24, 1983 [GB] United Kingdom ................ 8334497

[51] Int. Cl.$^4$ .................. C07D 405/04; C07D 311/68; A61K 31/35; A61K 31/40
[52] U.S. Cl. .................... 514/456; 514/278; 514/320; 514/409; 514/422; 546/15; 546/196; 548/407; 548/525; 549/399; 549/345
[58] Field of Search ................ 548/525, 407; 546/196, 546/15; 549/399, 345; 514/422, 320, 456, 278, 409

[56] References Cited

U.S. PATENT DOCUMENTS

| 4,366,163 | 12/1982 | Evans et al. ..................... 549/399 X |
| 4,446,113 | 5/1984 | Evans et al. ..................... 549/399 X |
| 4,481,214 | 11/1984 | Evans ............................. 549/399 X |
| 4,521,607 | 6/1985 | Oka et al. ........................ 549/361 X |
| 4,542,149 | 9/1985 | Evans et al. ..................... 546/196 X |
| 4,555,509 | 11/1985 | Evans et al. ..................... 548/525 X |

FOREIGN PATENT DOCUMENTS

| 0009912 | 4/1980 | European Pat. Off. . |
| 0028064 | 5/1981 | European Pat. Off. . |
| 28449 | 5/1981 | European Pat. Off. . |
| 0076075 | 4/1983 | European Pat. Off. . |
| 0091748 | 10/1983 | European Pat. Off. . |
| 95316 | 11/1983 | European Pat. Off. ............ 549/399 |
| 0093535 | 11/1983 | European Pat. Off. . |
| 0107423 | 5/1984 | European Pat. Off. . |
| 3040727 | 8/1981 | Fed. Rep. of Germany . |
| 632262 | 9/1982 | Switzerland . |

OTHER PUBLICATIONS

Lovgren, et al., Chem Abstracts, vol 87 (1977), entry 68075e.

Lap et al., Chem. Abst., 91:39260p-1979.
Lap et al., Aust. J. Chem. 32, 619-636,-1979.
Lovgren et al., Chem. Abst., 87:68057e,-1977.

Primary Examiner—Nicholas S. Rizzo
Assistant Examiner—William A. Teoli, Jr.
Attorney, Agent, or Firm—Jacobs & Jacobs

[57] ABSTRACT

Compounds of formula (I):

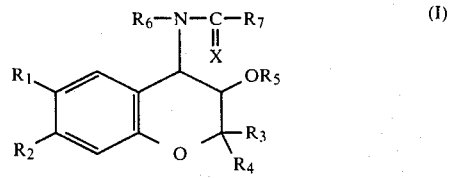

wherein:
either one of $R_1$ and $R_2$ is hydrogen and the other is selected from $C_{1-6}$ alkylcarbonyl, $C_{1-6}$ alkoxycarbonyl, $C_{1-6}$ alkylcarbonyloxy, $C_{1-6}$ alkylhydroxymethyl, nitro, cyano, chloro, trifluoromethyl, $C_{1-6}$ alkylsulphinyl, $C_{1-6}$ alkylsulphonyl, $C_{1-6}$ alkoxysulphinyl, $C_{1-6}$ alkoxysulphonyl, $C_{1-6}$ alkylcarbonylamino, $C_{1-6}$ alkoxycarbonylamino, $C_{1-6}$ alkylthiocarbonyl, $C_{1-6}$ alkoxy-thiocarbonyl, $C_{1-6}$ alkylthiocarbonyloxy, $C_{1-6}$ alkyl-thiolmethyl, formyl or aminosulphinyl, aminosulphonyl or aminocarbonyl, the amino moiety being optionally substituted by one or two $C_{1-6}$ alkyl groups, or $C_{1-6}$ alkylsulphinylamino, $C_{1-6}$ alkylsulphonylamino $C_{1-6}$ alkoxysulphinylamino or $C_{1-6}$ alkoxysulphonylamino or ethylenyl terminally substituted by $C_{1-6}$ alkylcarbonyl, nitro or cyano, or —C($C_{1-6}$ alkyl)NOH or —C($C_{1-6}$ alkyl)NNH$_2$, or one of $R_1$ and $R_2$ is nitro, cyano or $C_{1-3}$ alkylcarbonyl and the other is methoxy or amino optionally substituted by one or two $C_{1-6}$ alkyl or by $C_{2-7}$ alkanoyl;

8 Claims, No Drawings

CHROMANOL DERIVATIVES

The present invention relates to novel compounds having pharmacological activity, to a process for preparing them, to pharmaceutical compositions containing them, and to their use in the treatment of mammals.

U.S. Pat. No. 4,110,347, U.S. Pat. No. 4,251,532, U.S. Pat. No. 4,446,113, European Patent Publication No. 9912, European Patent Publication No. 28064 and European Patent Publication No. 76075 describe classes of 4-aminochroman-3-ol derivatives in which the amino function and the OH or alkyl or acyl derivative thereof are trans to one another. The compounds are described as having blood pressure lowering activity.

A class of chroman derivatives have now been discovered wherein the amino function and the OH or an alkyl or acyl derivative thereof are cis; these compounds have also been found to have blood pressure lowering activity.

Accordingly, the present invention provides a compound of formula (I):

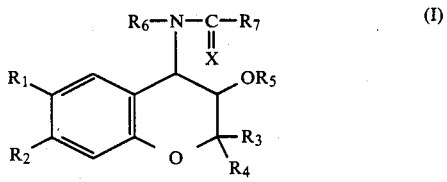

wherein: either one of $R_1$ and $R_2$ is hydrogen and the other is selected from the class of $C_{1-6}$ alkylcarbonyl, $C_{1-6}$ alkoxycarbonyl, $C_{1-6}$ alkylcarbonyloxy, $C_{1-6}$ alkylhydroxymethyl, nitro, cyano, chloro, trifluoromethyl, $C_{1-6}$ alkylsulphinyl, $C_{1-6}$ alkylsulphonyl, $C_{1-6}$ alkoxysulphinyl, $C_{1-6}$ alkoxysulphonyl, $C_{1-6}$ alkylcarbonylamino, $C_{1-6}$ alkoxycarbonylamino, $C_{1-6}$ alkyl-thiocarbonyl, $C_{1-6}$ alkoxy-thiocarbonyl, $C_{1-6}$ alkyl-thiocarbonyloxy, $C_{1-6}$ alkyl-thiolmethyl, formyl or aminosulphinyl, aminosulphonyl or aminocarbonyl, the amino moiety being optionally substituted by one or two $C_{1-6}$ alkyl groups, or $C_{1-6}$ alkylsulphonylamino, $C_{1-6}$ alkylsulphonylamino $C_{1-6}$ alkoxysulphinylamino or $C_{1-6}$ alkoxysulphonylamino or ethylenyl terminally substituted by $C_{1-6}$ alkylcarbonyl, nitro or cyano, or —C($C_{1-6}$ alkyl)-NOH or —C($C_{1-6}$ alkyl)NNH$_2$, or one of $R_1$ and $R_2$ is nitro, cyano or $C_{1-3}$ alkylcarbonyl and the other is methoxy or amino optionally substituted by one or two $C_{1-6}$ alkyl or by $C_{2-7}$ alkanoyl;

one of $R_3$ and $R_4$ is hydrogen or $C_{1-4}$ alkyl and the other is $C_{1-4}$ alkyl or $R_3$ and $R_4$ together are $C_{2-5}$ polymethylene;

$R_5$ is hydrogen, $C_{1-3}$ alkyl or $C_{1-8}$ acyl;

$R_6$ is hydrogen or $C_{1-6}$ alkyl; and $R_7$ is hydrogen, $C_{1-6}$ alkyl optionally substituted by hydroxy, $C_{1-6}$ alkoxy, $C_{1-6}$ alkoxycarbonyl or carboxy, $C_{1-6}$ alkyl substituted by halogen or $C_{2-6}$ alkenyl; $C_{1-6}$ alkyl substituted by amino optionally substituted by one or two $C_{1-6}$ alkyl groups which may be the same or different; amino optionally substituted by a $C_{1-6}$ alkyl or $C_{1-6}$ alkenyl group or by a $C_{1-6}$ alkanoyl group optionally substituted by up to three halo atoms, by a phenyl group optionally substituted by $C_{1-6}$ alkyl, $C_{1-6}$ alkoxy or halogen; or $C_{1-6}$ alkoxy, or phenoxy optionally substituted by $C_{1-6}$ alkyl, $C_{1-6}$ alkoxy or halogen; aryl or heteroaryl, either being optionally substituted by one or more groups or atoms selected from the class of $C_{1-6}$ alkyl, $C_{1-6}$ alkoxy, hydroxy, halogen, trifluoromethyl, nitro, cyano, $C_{1-12}$ carboxylic acyl, or amino or aminocarbonyl optionally substituted by one or two $C_{1-6}$ alkyl; or, when X is oxygen, $R_7$ is selected from the class of carboxy, $C_{1-6}$ alkoxycarbonyl, or aminocarbonyl optionally substituted by one or two $C_{1-6}$ alkyl groups which may be the same or different; or $R_6$ and $R_7$ together are $C_{3-4}$ polymethylene;

X is oxygen or sulphur; and the $R_6NCXR_7$ and $OR_5$ moieties are cis or, when one or the other of $R_1$ and $R_2$ and/or $R_7$ is an amino or an amino-containing group, a pharmaceutically acceptable salt thereof.

There is a group of compounds within formula (I) wherein $R_1$, $R_2$, $R_3$, $R_4$, $R_5$, $R_6$ and X are as hereinbefore defined and $R_7$ is hydrogen, $C_{1-6}$ alkyl optionally substituted by hydroxy, $C_{1-6}$ alkoxy, $C_{1-6}$ alkoxycarbonyl or carboxy, $C_{1-6}$ alkyl substituted by halogen or $C_{2-6}$ alkenyl; or together with $R_6$ is $C_{3-4}$ polymethylene.

When one of $R_1$ and $R_2$ is hydrogen, the other is often selected from the class of $C_{1-6}$ alkylcarbonyl, $C_{1-6}$ alkoxycarbonyl, $C_{1-6}$ alkylcarbonyloxy, $C_{1-6}$ alkylhydroxymethyl, nitro, cyano or chloro. In particular, when one of $R_1$ and $R_2$ is hydrogen, the other is preferably nitro, cyano, $C_{1-6}$ alkylcarbonyl or $C_{1-6}$ alkoxycarbonyl, most preferably nitro or cyano.

When one of $R_1$ and $R_2$ is hydrogen, it is preferred that $R_2$ is hydrogen.

When one of $R_1$ and $R_2$ is nitro, cyano or $C_{1-3}$ alkylcarbonyl the other is preferably amino optionally substituted by one or two $C_{1-6}$ alkyl or by $C_{2-7}$ alkanoyl. In particular, when one of $R_1$ and $R_2$ is nitro, cyano or $C_{1-3}$ alkylcarbonyl, the other is amino, methylamino, dimethylamino or acetylamino. Most preferably, one of $R_1$ and $R_2$ is nitro or cyano and the other is amino.

When one of $R_1$ and $R_2$ is nitro, cyano or $C_{1-3}$ alkylcarbonyl, it is preferred that $R_1$ is nitro, cyano or $C_{1-3}$ alkylcarbonyl.

The alkyl groups or alkyl moieties of alkyl-containing groups for $R_1$ or $R_2$ are, preferably, methyl or ethyl.

Favourably, $R_3$ and $R_4$ are both alkyl having from 1 to 4 carbon atoms including methyl, ethyl or n-propyl. In particular, they are both methyl or ethyl, preferably both methyl.

Suitable examples for $R_5$ when $C_{1-3}$ alkyl include methyl, ethyl, n- and iso-propyl, preferably methyl.

Suitable examples for $R_5$ when acyl include carboxylic acyl such as acetyl, propionyl and benzoyl.

$R_5$ is preferably hydrogen.

Suitable values for $R_6$, when $R_7$ and $R_6$ together are not $C_{3-4}$ polymethylene, include hydrogen, methyl, ethyl, n- and iso-propyl, n-, sec- and tert-butyl. Favourably, $R_6$ is hydrogen or methyl, most preferably hydrogen.

Examples of $R_7$, when $R_7$ and $R_6$ together are not $C_{3-4}$ polymethylene, include the following:

hydrogen, methyl, ethyl, n- and iso-propyl, n-, sec- and tert-butyl, methyl or ethyl substituted by carboxy or chloro, vinyl, prop-1-enyl, prop-2-enyl, 1-methylvinyl, but-1-enyl, but-2-enyl, but-3-enyl, 1-methylenepropyl, 1-methylprop-1-enyl, 1-methylprop-2-enyl, (in their E and Z forms where stereoisomerism exits), methyl or ethyl terminally substituted by hydroxy or methoxy. Favourably $R_7$ is methyl, ethyl, n- or iso-propyl or vinyl, in particular, methyl, hydroxymethyl and methoxymethyl. Preferably $R_7$ is methyl.

A group $(CH_2)_p NR_8 R_9$ where P is 1 to 6, and $R_8$ and $R_9$ are each independently hydrogen or $C_{1-6}$ alkyl. Examples of p include 1 and 2, in particular 1. Preferably $R_8$ and $R_9$ are each independently selected from hydrogen and methyl.

Amino optionally substituted by a methyl, ethyl, propyl or butyl alkyl or trichloroacetyl group or by a phenyl group optionally substituted by one methyl, methoxy or chloro group or atom, in particular amino, methylamino, and phenylamino optionally substituted in the phenyl ring by one methyl, methoxy or chloro group or atom.

Methoxy, ethoxy, n- and iso-propoxy, and phenoxy optionally substituted by one methyl, ethyl, methoxy, ethoxy, chloro or bromo group or atom, preferably methoxy, ethoxy, and phenoxy optionally substituted by one methyl, methoxy or chloro group or atom, in particular ethoxy. X is preferably oxygen in this case.

When X is oxygen: carboxyl, methoxycarbonyl, ethoxycarbonyl, aminocarbonyl, methylaminocarbonyl and dimethylaminocarbonyl, in particular ethoxycarbonyl or aminocarbonyl.

Examples of $R_7$ aryl include phenyl and naphthyl of which phenyl is preferred.

A sub-class of $R_7$ heteroaryl is 5- or 6-membered monocyclic or 9- or 10-membered bicyclic heteroaryl of which 5- or 6-membered monocyclic heteroaryl is preferred. In addition, 5- or 6-membered monocyclic or 9- or 10-membered bicyclic heteroaryl preferably contains one, two or three heteroatoms which are selected from the class of oxygen, nitrogen and sulphur and which, in the case of there being more than one heteroatom, are the same or different.

Examples of 5- or 6-membered monocyclic heteroaryl containing one, two or three heteroatoms which are selected from the class of oxygen, nitrogen and sulphur include furanyl, thiophenyl, pyrryl, oxazolyl, thiazolyl, imidazolyl and thiadiazolyl, and pyridinyl, pyridazinyl, pyrimidinyl, pyrazinyl and triazinyl. Preferred examples of such groups include furanyl, thiophenyl, pyrryl and pyridyl, in particular 2- and 3-furanyl, 2- and 3-pyrryl, 2- and 3-thiophenyl, and 2-, 3- and 4-pyridinyl.

Examples of 9- or 10-membered bicyclic heteroaryl containing one, two or three heteroatoms which are selected from the class of oxygen, nitrogen and sulphur include benzofuranyl, benzothiophenyl, indolyl and indazolyl, quinolinyl and isoquinolinyl, and quinazoninyl. Preferred examples of such groups include 2- and 3-benzofuranyl, 2- and 3-benzothiophenyl, and 2- and 3-indolyl, and 2- and 3-quinolinyl.

Preferably, the number of groups or atoms for optional substitution of aryl or heteroaryl is one, two, three or four.

Preferred examples of the groups or atoms for optional substitution of ary or heteroaryl include methyl, methoxy, hydroxy, chloro, nitro or cyano.

A sub-class of $R_7$ is phenyl or naphthyl or a 5- or 6-membered monocyclic or a 9- or 10-membered bicyclic heteroaryl, the phenyl or heteroaryl group being optionally substituted by one, two, three or four groups or atoms selected from the class of $C_{1-6}$ alkyl, $C_{1-6}$ alkoxy, halogen, trifluoromethyl, nitro or cyano.

A preferred sub-class of phenyl optionally substituted as hereinbefore defined is phenyl, 4-substituted phenyl, 3-substituted phenyl, 3,4-disubstituted phenyl and 3,4,5-trisubstituted phenyl. Particular examples of phenyl optionally substituted as hereinbefore defined include phenyl, 4-hydroxyphenyl, 4-fluorophenyl, 4-cyanophenyl, 3-nitrophenyl, 3,4-dichlorophenyl and 3,4,5-trimethoxyphenyl.

A preferred sub-class of 5- or 6-membered monocyclic or 9- or 10-membered bicyclic heteroaryl optionally substituted as hereinbefore defined is unsubstituted or mono-substituted 5- or 6-membered monocyclic or 9- or 10-membered bicyclic heteroaryl, in particular unsubstituted 5- or 6-membered monocyclic or 9- or 10-membered bicyclic heteroaryl.

X is preferably oxygen.

There is a favourable group of compounds within formula (I) of formula (II):

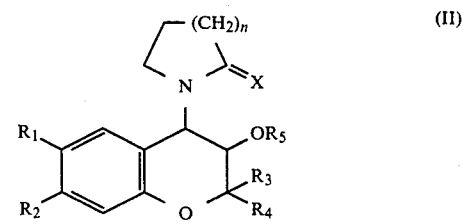

wherein n is 1 or 2 and the remaining variables are as defined in formula (I).

Suitable and preferred values for the variables are as described under formula (I).

It will be appreciated that there is a preferred sub-group of compounds within formula (I) of formula (III):

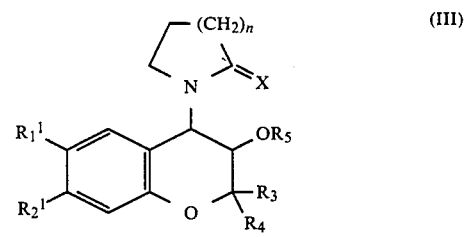

wherein one of $R_1^1$ and $R_2^1$ is hydrogen and the other is cyano or nitro and the remaining variables are as defined in formula (I).

Suitable and preferred values for the variables are as described under formula (I).

From the aforesaid it will be appreciated that there is a preferred compound within formula (III) of formula (IV):

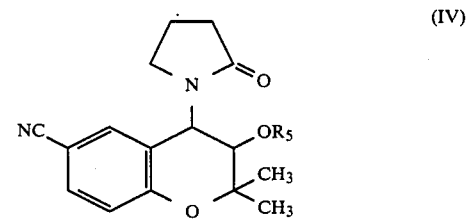

wherein the lactam and hydroxy groups are cis to each other.

Other examples of compounds of formula (I) include the compounds prepared in the Examples hereinafter.

There is a further sub-group of compounds within formula (II) of formula (V):

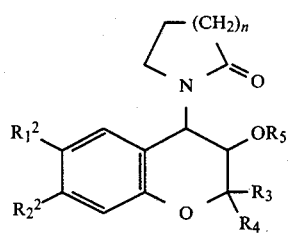

wherein: one of $R_1^2$ and $R_2^2$ is cyano or nitro and the other is amino optionally substituted as defined and the remaining variables are as defined in formula (I).

Favourably $R_1^2$ is cyano or nitro and $R_2^2$ is amino. Suitable and preferred values for the remaining variables are as described under formula (I).

There is a further group of compounds within formula (I) of formula (VI):

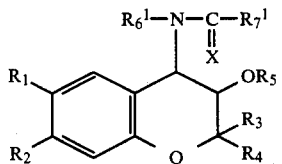

wherein $R_6^1$ is hydrogen or $C_{1-6}$ alkyl and $R_7^1$ is $C_{1-6}$ alkyl optionally substituted by hydroxy or methoxy and the remaining variables are as defined in formula (I).

Suitable and preferred values of the variables are as described for the corresponding variables in formula (I).

There is a favourable sub-group of compounds within formula (VI) of formula (VII):

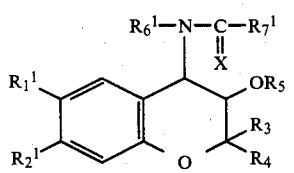

wherein $R_1^1$ and $R_2^1$ are as defined in formula (III) and the remaining variables are as defined in formulae (I) and (VI).

Suitable and preferred values for the variables are as described for the corresponding variables under formula (I).

A preferred sub-group of compounds within formula (VII) is of formula (VIII):

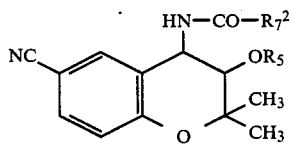

wherein $R_7^2$ is $C_{1-4}$ alkyl, preferably methyl. Preferably $R_5$ is hydrogen.

The compounds of the formula (I) are asymmetric and, therefore, can exist as stereoisomers. The present invention extends to all such stereoisomers individually and as mixtures, such as racemic modifications.

The present invention also provides a process for the preparation of a compound of formula (I) which process comprises the reaction of a compound of formula (IX):

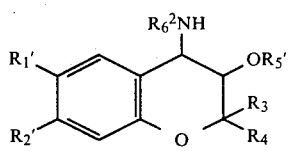

(i) with $R_7^2COQ_1$ wherein the $R_6^2NH$ and $OR_5$ moieties are cis; and $R_1'$ and $R_2'$ are $R_1$ and $R_2$ respectively or a group or atom convertible thereto;

$R_5'$ is $R_5$ or a group or atom convertible thereto;

$R_6^2$ is hydrogen or $C_{1-6}$ alkyl;

$R_7^2$ is $R_7$ other than amino optionally substituted as hereinbefore defined, or a group convertible thereto or (when $R_6^2$ is hydrogen), $Q_2(CH2)_{n+2}-$ or a metal salt thereof;

$Q_1$ and $Q_2$ are leaving groups; and thereafter in the case where $R_7^2$ is a group convertible to $R_7$ which is other than amino optionally substituted as hereinbefore defined, converting $R_7^2$ to other $R_7$ which is also other than amino optionally substituted as hereinbefore defined; cyclising the compound formed when $R_7^2$ is $Q_2(CH2)_{n+2}-$; or (ii) with a compound of formula:

$$X=C=N.R_{10}$$

wherein $R_{10}$ is hydrogen, $C_{1-6}$ alkyl, $C_{1-6}$ alkenyl, $C_{1-6}$ alkanoyl optionally substituted by up to three halo atoms or phenyl optionally substituted by $C_{1-6}$ alkyl, $C_{1-6}$ alkoxy or halogen; and X is oxygen or sulphur, and thereafter when $R_{10}$ is hydrogen, optionally converting $R_{10}$; and thereafter in the case where $R_1'$ or $R_2'$ is a group or atom convertible into $R_1$ or $R_2$, converting the group or atom into $R_1$ or $R_2$; optionally converting $R_1$, $R_2$ or $R_5$ in the resulting compound of formula (I) into another $R_1$, $R_2$ or $R_5$; optionally converting $R_6^2$ when hydrogen to $C_{1-6}$ alkyl; and optionally thiating the carbonyl group of any $R_6NCOR_7$ group in the resulting compound of formula (I) where $R_7$ is other than carboxy, $C_{1-6}$ alkoxycarbonyl or aminocarbonyl optionally substituted as hereinbefore defined to give another compound of formula (I), wherein X is sulphur; and, when the resulting compound of formula (I) contains a salifiable group, optionally forming a pharmaceutically acceptable salt thereof.

In process variant (i), the leaving group $Q_1$ is a group that is displaceable by a primary or secondary amino nucleophile. Examples of such a group include $C_{2-9}$ acyloxy, such as $C_{1-4}$ alkylcarbonyloxy, and, preferably halogen, such as chloro and bromo. When the leaving group $Q_1$ is either of these examples, the acylating agent is either an acid anhydride or an acid halide. When it is acid anhydride, it may be a mixed or simple anhydride. If it is a mixed anhydride, it may be prepared in situ from a carboxylic acid and an acid halide, although this is much less preferred than using the halide itself. A further example of the leaving group $Q_1$ is a hydroxy group although this is less preferred than the leaving groups previously mentioned.

In process variant (i), when $R_7$ in the desired compound of formula (I) is an $R_7$ substituted alkyl group as hereinbefore defined it is preferred that $R_7^2$ is a group convertible to the $R_7$ substituted alkyl group as hereinbefore defined in particular that it is $C_{1-6}$ alkyl substituted by halo, especially bromo. The $R_7^2$ halo substituent in the resultant compound of process variant (i) may be converted to an $R_7$ substituent which is amino optionally substituted as hereinbefore defined by a conventional amination reaction with ammonia or a corresponding alkyl- or dialkylamine.

Less favourably $R_7^2$ may be $C_{1-6}$ alkyl substituted by protected amino, protected $C_{1-6}$ alkyl amino or amino substituted by two independent $C_{d\ 1-6}$ alkyl groups, it being necessary to protect the $R_7$ amino function in process variant (i). Particular examples of such a group $R_7^2$ include a group $(CH_2)_p NR_8'R_9'$ where p is 1 to 6, and $R_8'$ and $R_9'$ together are a divalent protecting group, one of $R_8'$ and $R_9'$ is methyl and the other is a monovalent protecting group, or each of $R_8'$ and $R_9'$ is methyl. Suitable protecting groups and deprotection conditions to achieve the subsequent $R_7^2$ to $R_7$ conversion without breaking the $R_6.N.CO.R_7$ amide bond will be readily apparent to the skilled man.

When the acylating agent is an acid anhydride, the acylation of the compound of formula (IX) is, preferably, carried out using the anhydride as the solvent in the presence of an acid acceptor, such as sodium acetate, or, preferably, triethylamine.

When the acylating agent is an acid halide, the acylation of the compound of formula (IX) is, preferably, carried out in a medium such as chloroform or dichloromethane, in the presence of an acid acceptor, such as triethylamine, trimethylamine, pyridine, picoline or calcium, potassium or sodium carbonate.

In process variant (i), when $R_7^2$ is $C_{1-6}$ alkoxy, phenoxy optionally substituted as hereinbefore defined, or $C_{1-6}$ alkoxycarbonyl, examples of the leaving group $Q_1$ include halogen such as chloro or bromo. Acylation is then preferably carried out under the reaction conditions described hereinbefore for corresponding $Q_1$ groups.

When $R_5'$ in a compound of formula (IX) in process variant (i) is hydroxy, there is a risk of a side-reaction between the hydroxy group and the acylating agent but this may be minimised by effecting the reaction at relatively low temperatures, e.g. at below 10° C. Alternatively, $R_5'$ may be $C_{1-7}$ acyloxy in a compound of formula (IX) and, after reaction with the acylating agent be converted into hydroxy, as described hereinafter. It is however, preferred that the reaction is controlled conventionally as described hereinbefore such, that only the amine, $R_6NH-$, is acylated.

The cyclisation reaction when $R_7^2$ is $Q_2(CH_2)_{n+2}$ is preferably carried out in an inert solvent such as tetrahydrofuran.

When a metal salt of $R_7^2$ when $Q_2(CH_2)_{n+2}$ is used, the sodium salt is preferred.

In process variant (ii), when $R_{10}$ is $C_{1-6}$ alkyl, $C_{1-6}$ alkonyl optionally substituted as hereinbefore defined, or phenyl optionally substituted as hereinbefore defined, the reaction of the compound of formulae (IX) is, preferably, carried out in a solvent, such as methylene chloride, at below room temperature, in particular below 10° C.

When $R_{10}$ is hydrogen, the reaction of the compound of formula (IX) is, preferably, carried out using a corresponding alkali metal cyanate or thiocyanate, for example that of sodium or potassium, in an aqueous medium optionally methanolic acidified with a mineral acid, such as dilute hydrochloric acid. A slightly elevated temperature such as 50° to 90° C. is apt.

Conversions of an aromatic group or atom into one of the class of substituents as defined hereinbefore are generally known. For example, it is preferred, when carrying out the reaction, to protect any unsubstituted terminal amino moieties, such as when the $R_1/R_2$ is amino, with a protecting agent. Examples of protecting agents include acyl groups, such as acetyl. Removal of the acyl protecting agent is carried out by base hydrolysis.

If it is desired to protect an amino group in the presence of a cyano group then a more suitable method is to use a trifluoroacetyl protecting group which may be removed by mild hydrolysis. A further suitable method of deprotection of a protected amino group in the presence of a cyano group is to utilise a benzyloxycarbonyl or p-nitrobenzyloxycarbonyl protecting group which groups may be removed by mild catalytic hydrogenolysis. Benyloxycarbonyl amino and p-nitrobenzyloxycarbonylamino groups may be formed by reaction of the appropriate chloride with the free amine function.

In addition a hydrogen atom may be replaced by a nitro group by nitrating in a known manner a compound of formula (V), wherein one of $R_1'$ and $R_2'$ is hydrogen and the other is acetamido, followed by hydrolysing the compound, converting the resulting amine into a diazonium salt, and finally decomposing it, leaving a compound of formula (I), wherein one of $R_1$ and $R_2$ is hydrogen and the other is nitro.

It is however preferred that any conversions are carried out at an earlier stage as mentioned hereafter.

An $R_6^2$ hydrogen atom may be converted to $R_6^2$ $C_{1-6}$ alkyl group by conventional amine alkylation, preferably using an alkyl halide in an inert solvent, such as dimethylformamide under basic conditions, using a base such as potassium carbonate. A more preferred method, however is by conventional reductive amination using the corresponding alkanoyl halide followed by reduction using sodium cyanoborohydride.

Preferably, an $R_5$ alkylating agent is an alkyl iodide, the reaction being carried out in an inert solvent, such as toluene, in the presence of a base, such as potassium t-butoxide.

Preferably, an $R_5$ acylating agent is carboxylic acid or a derivative thereof, such as an anhydride, the reaction being carried out in a non-hydroxylic solvent in the presence of a condensation promoting agent, such as dicyclohexyl-carbodiimide or triethylamine.

$R_5'$ may be a protecting group such as a $C_{1-6}$ alkyl or $C_{1-8}$ acyl group or, more suitably, tetrahydropyran-2-yl. Such groups may be removed by conventional hydrolysis.

The leaving group $Q_2$ is a group that is displaceable by a secondary amino nucleophile adjacent a carbonyl function. A preferred example is chloro.

The thiation reaction is preferably carried out with conventional thiation agents, such as hydrogen sulphide, phosphorous pentasulphide and Lawesson's reagent (p-methoxyphenylthiophosphine sulphine dimer). The use of hydrogen sulphide and phosphorus pentasulphide may lead to side-reactions and, therefore, the use of Lawesson's reagent is preferred.

The thiation reaction conditions are conventional for the thiation agent employed. For example, the use of hydrogen sulphide is, preferably, acid catalysed by, for example, hydrogen chloride in a polar solvent, such as acetic acid or ethanol. The preferred use of Lawesson's reagent is carried out at temperatures from room temperatures to reflux in a dry solvent, such as toluene or methylene chloride.

When X is sulphur and $R_1$ and $R_2$ is a carbonyl-containing group in formula (I), then it is preferred to use the corresponding compound of formula (V), wherein $R_1'$ or $R_2'$ is a protected carbonyl-containing group, in the thiation reaction, and afterwards to convert the protected carbonyl-containing group into the required carbonyl-containing group for $R_1$ or $R_2$. Without such protection, the additional carbonyl group may give rise to a competing side-reaction. Examples of preferred carbonyl protecting groups include ketalising agents, which may be added and removed in conventional manner.

When one of $R_1$ and $R_2$ in the compound of formula (I) so obtained is an amino or an amino-containing group, the optional formation of a pharmaceutically acceptable salt thereof may be carried out in accordance with conventional procedures.

Intermediates of the formula (IX) wherein $R_6$ is hydrogen are prepared from the trans bromohydrin or an alkylated or acylated derivative thereof, of the formula (X):

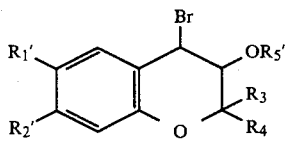

by reaction with sodium azide in dimethylformamide to form the corresponding cishydroxy-/acyloxy-/alkoxy-azide which may be reduced, preferably by catalytic reduction with hydrogen/palladium to give a compound of formula (IX).

It is preferred that $R_5'$ is other than hydrogen in formula (X) i.e. the $R_5$ hydrogen atom is protected by alkylation or acylation or other protecting group. One preferred example of a protecting group is tetrahydropyran-2-yl. The protecting group is normally removed after the reduction step.

If $R_5'$ is hydrogen in formula (X) a mixture of cis and trans hydroxyazides are formed which can then be separated conventionally, usually by chromatography.

Compounds of formula (IX) wherein $R_6^2$ is other than hydrogen can be formed by conventional amine alkylation or acylation followed by reduction.

Compounds of formula (X) where $R_5'$ is hydrogen are prepared by reaction of a compound of formula (XI):

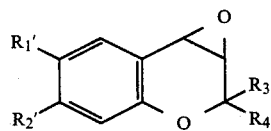

with hydrogen bromide. Compounds of formula (X) wherein $R_5'$ is other than hydrogen may be prepared by conventional alkylation/acylation procedures as hereinbefore described.

Intermediates of the formulae (IX) are novel and thus form an aspect of the present invention.

Compounds of formula (XI) are known and may be prepared in accordance with processes described in the aforementioned U.S. Patents and European Patent Publications.

As mentioned previously, the compounds of formula (I) exist in optically active forms, and the processes of the present invention produce mixtures of such forms. The individual isomers may be separated one from the other by chromatography using a chiral phase.

As mentioned previously, the compounds of formula (I) have been found to have blood-pressure lowering activity. They are therefore useful in the treatment of hypertension.

The present invention accordingly provides a pharmaceutical composition which comprises a compound of formula (I) and a pharmaceutically acceptable carrier. In particular, the present invention provides an anti-hypertensive pharmaceutical composition which comprises an anti-hypertensive effective amount of a compound of formula (I) and a pharmaceutically acceptable carrier.

The compositions are preferably adapted for oral administration. However, they may be adapted for other modes of administration, for example parenteral administration for patients suffering from heart failure.

In order to obtain consistency of administration it is preferred that a composition of the invention is in the form of a unit-dose. Suitable unit dose forms include tablets, capsules and powders in sachets or vials. Such unit does forms may contain from 1 to 100 mg of a compound of the invention and more usually from 2 to 50 mg, for example 5 to 25 mg such as 6, 10, 15 or 20 mg. Such compositions may be administered from 1 to 6 times a day, more usually from 2 to 4 times a day, in a manner such that the daily does is from 5 to 200 mg for a 70 kg human adult and more particularly from 10 to 100 mg.

The compositions of the invention may be formulated with conventional excipients, such as a filter, a disintegrating agent, a binder, a lubricant, a flavouring agent. They are formulated in conventional manner, for example in a manner similar to that used for known anti-hypertensive agents, diuretics and $\beta$-blocking agents.

The present invention further provides a compound of formula (I) for use in the treatment of hypertension.

The present invention yet further provides a method of treating hypertension in mammals including man, which comprises administering to the suffering mammal an anti-hypertensive effective amount of a compound of formula (I) or a pharmaceutical composition of the invention.

The following examples relate to the preparation of compounds of formula (I) and the following descriptions relate to the preparation of intermediates thereto.

Description 1

Trans-4-Bromo-6-cyano-3,4-dihydro-2,2-dimethyl-2H-benzo[b]pyran-3-ol tetrahydropyranyl ether

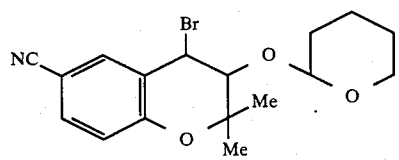

To a stirred solution of 6-cyano-3,4-epoxy-3,4-hydro-2,2-dimethyl-2H-benzo[b]pyran (20.1 g, the preparation of which is described in European Patent Specification number 0 009 912) in carbon tetrachloride (500 mL) was added dropwise, 45% HBr (40 mL) at room temperature. After 2 hours of stirring, the carbon tetrachloride was washed with water and sodium bicarbonate solution before drying over anhydrous magnesium sulphate. Filtration and evaporation gave a pale yellow solid (24.6 g). A small portion of this was recrystallised from ethyl acetate-pentane to give trans-4-bromo-6-cyano-3,4-dihydro-2,2-dimethyl-2H-benzo[b]pyran-3-ol as pale yellow crystals of mp 111°–112° C.

The bromohydrin (12 g), dihydropyran (25 ml) and concentrated HCl (3 drops) were stirred at room temperature for 2 days. The mixture was poured into water and extracted with ethyl acetate. The organic phase was washed with water, and sodium bicarbonate solution before drying over anhydrous magnesium sulphate. Filtration and evaporation gave a gum which on trituration with pentane yielded the crude title compound as a sticky white solid (14.25 g).

Description 2

4-Azido-6-cyano-3,4-dihydro-2,2-dimethyl-2H-benzo[b]pyran-3-ol tetrahydropyranyl ether

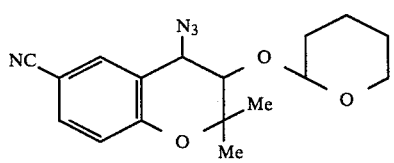

The crude tetrahydropyranyl bromide of demonstration 1 (14 g) and sodium azide (4 g) were stirred in N,N-dimethyl-formamide (50 mL) for 24 hours. The mixture was poured into water and extracted with ethyl acetate. The ethyl acetate was washed with water and brine before drying over anhydrous magnesium sulphate. Removal of drying agent and evaporation gave the compound of demonstration 2 as an oil (13.5 g), IR (film) 2100, 2225 cm$^{-1}$. The oil solidified on trituration with pentane.

Description 3

4-Amino-6-cyano-3,4-dihydro-2,2-dimethyl-2H-benzo[b]pyran-3-ol tetrahydropyranyl ether

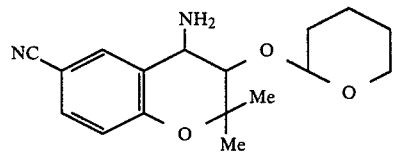

The azide of demonstration 2 (7.50 g) in ethanol (150 mL) was shaken in an atmosphere of hydrogen, together with 5% Pd/C (500 mg) for 25 hr. Filtration and evaporation gave a yellow foam (6.29 g). IR examination showed a trace of the absorption at 2100 cm$^{-1}$ present in the compound of demonstration 2.

Mass spectrum MH$^+$ at m/z 303.1707.

Calculated for $C_{17}H_{22}N_2O_3.H^+$ 303.1708.

Description 4 cis-4-Amino-6-cyano-3,4-dihydro-2,2-dimethyl-2H-benzo[b]pyran-3-ol

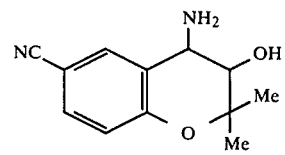

Trans-4-bromo-6-cyano-3,4-dihydro-2,2-dimethyl-2H-benzo[b]pyran-3-ol (3.94 g, prepared as described in demonstration 1) was stirred with sodium azide (3.0 g) in dimethyl formamide (30 mL) for 2 hours at room temperature. The reaction mixture was poured into water and extracted with ethyl acetate. The ethyl acetate layer was washed with water and brine and dried over anhydrous magnesium sulphate. Filtration and evaporation gave a gum (3.85 g).

This hydroxy-azide (1.5 g) was dissolved in dimethyl formamide (10 mL) and concentrated HCl (2 mL), and treated with zinc dust (1 g) during 10 mins. The mixture was filtered, diluted with water and extracted with ethyl acetate. The aqueous phase was basified and extracted via ethyl acetate to furnish a basic fraction which was chromatographed (chromatotron, ascending concentrations of ethyl acetate (30→100%) in pentane, flow rate 6 mL/min, silica gel) to give the title compound (305 mg) as a powdery solid of mp 143°–144° from ethyl acetate.

Mass spectrum M$^+$ at m/z 218.1054 calcd for $C_{12}H_{14}N_2O_2$ 218.1055.

The other major fraction contained the trans-isomer (350 mg), previously described in European Patent application No. 0076 075.

EXAMPLE 1

6-Cyano-3,4-dihydro-2,2-dimethyl-cis-4-(2-oxo-1-pyrrolidinyl)-2H-benzo[b]pyran-3-ol E1

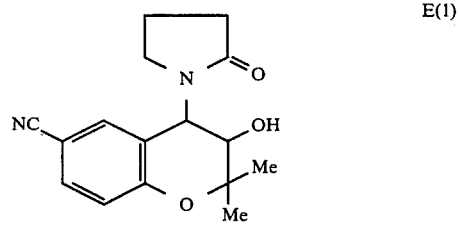

E(1)

The protected amine of demonstration 3 (5.91 g) and triethylamine (2.18 mL) were stirred in dichloromethane (60 mL) with cooling to 0° C. Chlorobutyryl chloride (2.25 mL) was added dropwise and on completion of the addition the reaction was stirred for 2 hours at room temperature. Addition of water and separation of the layers was followed by washing of the organic layer with brine. After the organic layer was dried over anhydrous MgSO$_4$, it was filtered and evaporated to give an oil (7.35 g).

This material was treated with conc HCl (2 mL) and water (2 mL) in ethanol (25 mL) during 2 hr. The solution was poured into water and extraction via ethyl acetate gave a yellow gum (4.50 g). It was purified by chromatography, and recrystallization from ethyl acetate, to give the 4-(4'-chlorobutyrylamino)-compound as crystals of mp 172°-173° C.

The crude chlorobutyrylamino compound (484 mg) was dissolved in dry tetrahydrofuran (25 mL) and treated, under nitrogen, with sodium hydride (48 mg, 80% dispersion in oil). After 4 hr at room temperature the reaction mixture was treated by cautious addition of water (200 mL). Extraction via ethyl acetate gave a cream coloured solid (340 mg). One recrystallization from ethyl acetate furnished the title compound (173 mg) of mp 216°-216.5° C.

IR (KBr disc) 2235, 1680 cm$^{-1}$.

Mass spectrum M+-H$_2$O at m/z 268.1212 calcd for C$_{16}$H$_{18}$N$_2$O$_3$ 268.1212.

NMR (CDCl$_3$) δ 1.36 (3H); 1.49 (3H); 2.12 (2H, m); 2.54 (2H, m); 2.79 (1H, br m, exchangeable); 3.34 (1H, m); 3.74 (1H, m); 3.88 (1H, q, collapsing to d 3.5 Hz on addition of D$_2$O); 5.41 (1H, d, J=3.5 Hz); 6.94 (1H, d, J=8.5 Hz); 7.24 (1H, narrow m); 7.48 (1H, m, J=8.5 Hz visible).

EXAMPLE 2

Cis-4-Acetylamino-6-cyano-3,4-dihydro-2,2-dimethyl-2H-benzo[b]pyran-3-ol (E2)

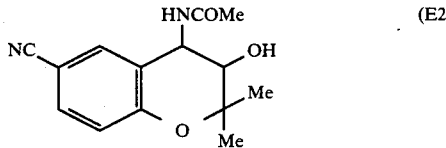

To the cis-aminoalcohol, obtained in demonstration 4 and other runs (313 mg) and triethylamine (0.21 mL), in dichloromethane (20 mL) was added acetyl chloride (0.104 mL) with vigorous stirring. The stirring was continued for 0.5 hr before the reaction mixture was washed with water, and dried over anhydrous magnesium sulphate. Filtration and evaporation gave a yellow foam which was purified by chromatography (chromatotron, ethyl acetate-pentane gradient elution, flow rate 6 mL/min, silica gel), and recrystallized from ethyl acetate to give the title compound (53 mg) of mp 193°-194° C.

Mass spectrum M+-18 at m/z 242.1057 Calculated for C$_{14}$H$_{16}$N$_2$O$_3$ 242.1055.

EXAMPLE 3

Cis-4-Benzoylamino-6-cyano-3,4-dihydro-2,2-dimethyl-2H-benzo[b]pyran-3-ol

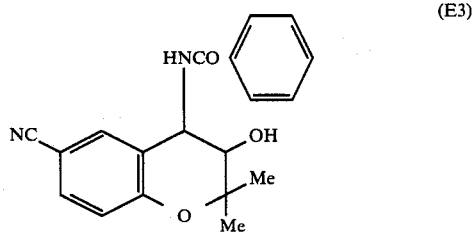

The compound of Example 3 was prepared in an analogous manner to that described in Example 2, using benzoyl chloride. Recrystallisation of the crude product from ethyl acetate-pentane gave the compound of Example 3 as crystals of m.p. 158°-159.5° C.

NMR (CDCl$_3$) δ 1.38 (3H, s), 1.53 (3H, s), 2.46 (1H, irreg m) exchangeable with D$_2$O, 3.83 (1H, irreg m) collapsing to d, J=4 Hz on addition of D$_2$O, 5.60 (1H, q, J=8, 4 Hz) very slowly, exchanging with D$_2$O to give d, J=4 Hz, 6.92 (1H, d, J=9 Hz) overlapped by, 7.05 (1H, d, J=8 Hz) very slowly exchanging with D$_2$O, 7.33-8.05 (7H, series of m).

Mass spectrum M+-18 at m/z 304.1222.

Calculated for C$_{19}$H$_{16}$N$_2$O$_2$ 304.1212.

EXAMPLE 4

Cis-6-Cyano-3,4-dihydro-2,2-dimethyl-4-(N-methylureido)-2H-benzo[b]pyran-3-ol

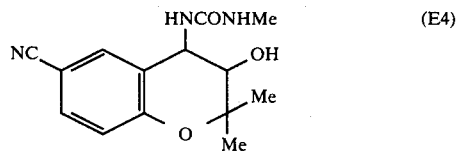

To the cis-aminoalcohol from demonstration 4 (0.20 g) dissolved in dichloromethane (10 mL), and cooled in an ice bath, was added methyl isocyanate (0.05 g). The stirred solution was allowed to attain room temperature and stirring was continued for 68 h. The solution was evaporated and a solid obtained which was recrystallised from ethyl acetate-pentane to give the title compound (63 mg) of m.p. 135°-137° C.

NMR (CDCl$_3$+D$_2$O) δ 1.34 (3H, s), 1.48 (3H, s), 2.83 (3H, s), 3.70 (1H, d, J=4 Hz), 5.23 (1H, d, J=4 Hz), 6.87 (1H, d, J=9 Hz), 7.45 (1H, q, J=9,2 Hz), 7.56 (1H, narrow m).

Mass Spectrum M+-18 at m/z 257.1160.

Calculated for C$_{14}$H$_{15}$N$_3$O$_2$ 257.1164.

Pharmacological Data

Systolic blood pressures were recorded by a modification of the tail cuff method described by I M Claxton, M G Palfreyman, R H Poyser, R L Whiting, European Journal of Pharmacology, 37, 179 (1976).

A W+W BP recorder, model 8005, was used to display pulses prior to all measurements rats were placed in a heated environment (33.5±0.5° C.) before transfer to a restraining cage. Each determination of blood pressure was the mean of at least 6 readings. Spontaneously hypertensive rats (ages 12-18 weeks) with systolic blood pressures >170 mmHg were considered hypertensive.

| | Time Post Dose Hours | % Change in Systolic Blood Blood | % Change in Heart Rate |
|---|---|---|---|
| Compound of Example 1 | | | |
| 6 rats | | | |
| Dose 1 mg/kg | 1 | 0 ± 6 | −2 ± 3 |
| p.o. | 2 | −2 ± 7 | −7 ± 3 |
| Initial Blood Pressure | 4 | −18 ± 6 | −1 ± 5 |
| 225 ± 13 mmHg | 6 | −23 ± 7 | 1 ± 2 |
| Initial Heart Rate | 24 | 2 ± 4 | 0 ± 5 |
| 463 ± 11 beats/min | | | |
| Compound of Example 2 | | | |
| 6 rats | | | |
| Dose 10 mg/kg | 1 | −48 ± 5* | −2 ± 2 |
| p.o. | 2 | −15 ± 7 | −5 ± 2 |
| Initial Blood Pressure | 4 | −35 ± 5* | −4 ± 2 |
| 242 ± 5 | 6 | −34 ± 3* | −4 ± 2 |
| Initial Heart Rate | | | |

-continued

| Time Post Dose Hours | % Change in Systolic Blood Blood | % Change in Heart Rate |
|---|---|---|
| 482 ± 5 | | |

*At 1 hour 2 rats had no measurable pulse
At 4 hours 1 rat had no measurable pulse Toxicity No toxic effects were observed in the above tests.

I claim:

1. A compound of formula (I)

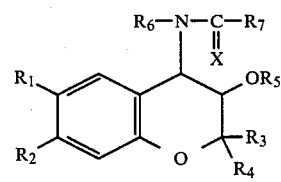
(I)

wherein:
either one of R₁ and R₂ is hydrogen and the other is C₁₋₆ alkylcarbonyl, C₁₋₆ alkoxycarbonyl, C₁₋₆ alkylcarbonyloxy, C₁₋₆ alkylhydroxymethyl, nitro, cyano, chloro, trifuoromethyl, C₁₋₆ alkylsulphinyl, C₁₋₆ alkylsulphonyl, C₁₋₆ alkoxysulphinyl, C₁₋₆ alkoxysulphonyl, C₁₋₆ alkylcarbonylamino, C₁₋₆ alkoxycarbonylamino, C₁₋₆ alkylthiocarbonyl, C₁₋₆ alkoxy-thiocarbonyl, C₁₋₆ alkyl-thiocarbonyloxy, C₁₋₆ alkyl-thiolmethyl, formyl or aminosulphinyl, aminosulphonyl or aminocarbonyl, the amino moiety being unsubstituted or substituted by one or two C₁₋₆ alkyl groups, or C₁₋₆ alkylsulphinylamino, C₁₋₆ alkylsulphonylamino, C₁₋₆ alkoxysulphinylamino or C₁₋₆ alkoxysulphonylamino or ethylenyl terminally substituted by C₁₋₆ alkylcarbonyl, nitro or cyano, or —C(C₁₋₆ alkyl)NOH or —C(C₁₋₆ alkyl)NNH₂, or one of R₁ and R₂ is nitro, cyano or C₁₋₃ alkylcarbonyl and the other is methoxy or amino unsubstituted or substituted by one or two C₁₋₆ alkyl or C₂₋₇ alkanoyl; one of R₃ and R₄ is hydrogen or C₁₋₄ alkyl and the other is C₁₋₄ alkyl or R₃ and R₄ together are C₂₋₅ polymethylene;
R₅ is hydrogen, C₁₋₃ alkyl or C₁₋₈ acyl;
R₆ is hydrogen or C₁₋₆ alkyl; and
R₇ is hydrogen, C₁₋₆ alkyl unsubstituted or substituted by hydroxy, C₁₋₆ alkoxy, C₁₋₆ alkoxycarbonyl or carboxy, C₁₋₆ alkyl substituted by halogen or C₂₋₆ alkenyl; C₁₋₆ alkyl substituted by amino unsubstituted or substituted by one or two C₁₋₆ alkyl groups which may be the same or different; amino unsubstituted or substituted by a C₁₋₆ alkyl or C₁₋₆ alkenyl group or by a C₁₋₆ alkanoyl group unsubstituted or substituted by up to three halo atoms, by a phenyl group unsubstituted or substituted by C₁₋₆ alkyl, C₁₋₆ alkoxy or halogen; or C₁₋₆ alkoxy, or phenoxy unsubstituted or substituted by C₁₋₆ alkyl, C₁₋₆ alkoxy or halogen; phenyl or naphthyl, either being unsubstituted or substituted by one or more C₁₋₆ alkyl, C₁₋₆ alkoxy, fluoro, chloro or bromo, trifluoromethyl, nitro, cyano, acetyl, propionyl and benzoyl, or amino or aminocarbonyl unsubstituted or substituted by one or two C₁₋₆ alkyl; or, when X is oxygen, R₇ is carboxy, C₁₋₆ alkoxycarbonyl, aminocarbonyl unsubstituted or substituted by one or two C₁₋₆ alkyl groups which may be the same or different; or
R₆ and R₇ together are C₃₋₄ polymethylene;
X is oxygen or sulphur; and the R₆NCXR₇ and OR₅ moieties are cis or, when one or the other of R₁ and R₂ and/or R₇ is an amino or an amino-containing group, a pharmaceutically acceptable salt thereof.

2. A compound according to claim 1 of formula (II):

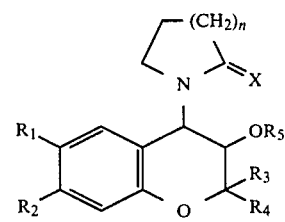
(II)

wherein n is 1 or 2.

3. A compound according to claim 2 of formula (II):

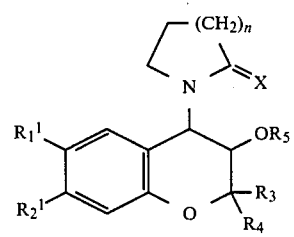
(III)

wherein one of R₁¹ and R₂¹ is hydrogen and the other is cyano or nitro.

4. A compound according to claim 1 of formula (VI):

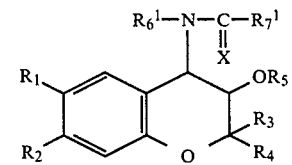
(VI)

wherein R₆¹ is hydrogen or C₁₋₆ alkyl and R₇¹ is C₁₋₆ alkyl unsubstituted or substituted by hydroxy or methoxy.

5. A compound according to claim 4 of formula (VII):

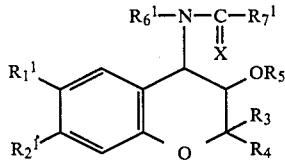
(VII)

wherein one of R₁' and R₂' is hydrogen and the other is cyano or nitro.

6. 6-Cyano-3,4-dihydro-2,2-dimethyl-cis-4-(2-oxo-1-pyrrolidinyl)-2H-benzo[b]pyran-3-ol, cis-4-acetylamino-6-cyano-3,4-dihydro-2,2-dimethyl-2H-benzo[b]pyran-3-ol, cis-4-benzoylamino-6-cyano-3,4-dihydro-2,2-dimethyl-2H-benzo[b]pyran-3-ol or cis-6- cyano-3,4-dihydro-2,2-dimethyl-4-(N-methylureido)-2H-benzo-[b]pyran-3-ol.

7. A pharmaceutical composition for treatment of hypertension in mammals, which comprises an anti-hypertensive effective amount of a compound according to claim 1 or a pharmaceutically acceptable salt thereof and a pharmaceutically acceptable carrier.

8. A method of treating hypertension in mammals, which comprises administering to a mammal in need thereof an anti-hypertensive effective amount of a compound according to claim 1 or a pharmaceutically acceptable salt thereof.

* * * * *